United States Patent [19]

Siegemund et al.

[11] 3,981,927

[45] Sept. 21, 1976

[54] 1,2,2,2-TETRAFLUOROETHYL ETHERS AND PROCESS FOR PREPARING THEM

[75] Inventors: Günther Siegemund, Hofheim, Taunus; Roman Muschaweck, Frankfurt am Main, both of Germany

[73] Assignee: Hoechst Aktiengesellschaft, Frankfurt am Main, Germany

[22] Filed: Aug. 8, 1974

[21] Appl. No.: 495,897

[30] Foreign Application Priority Data

Aug. 10, 1973 Germany............................ 2340560

[52] U.S. Cl...................... 260/614 F; 260/561 HL; 260/615 A; 260/615 F; 424/342
[51] Int. Cl.²................... C07C 43/00; C07C 43/12
[58] Field of Search................................ 260/614 F

[56] References Cited

UNITED STATES PATENTS 3,764,706   10/1973   Terrell .............................. 424/342

FOREIGN PATENTS OR APPLICATIONS 1,076,113   2/1960   Germany....................... 260/614 F

OTHER PUBLICATIONS

Siegemund, Chem. Abst., 80, 1974, 3031y–Chem. Ber., 1973, 106(9) 2960–2968.
Terrell et al., J. Med. Chem., 14, 517–519 (1971).

*Primary Examiner*—Howard T. Mars
*Attorney, Agent, or Firm*—Curtis, Morris & Safford

[57] ABSTRACT

1,2,2,2-Tetrafluoroethyl ethers and process for preparing them; the compounds are useful inhalation anesthetics which are distinguished by shorter recovery times.

3 Claims, No Drawings

1,2,2,2-TETRAFLUOROETHYL ETHERS AND PROCESS FOR PREPARING THEM

It is known to prepare the 1,2,2,2-tetrafluoroethyl-trifluoromethyl ether of the formula $CF_3CHF-O-CF_3$ [Zh. Obshch. Kim. 34, 2802 (1964); C.A. 61, 115969] by fixation of hydrogen fluoride on the trifluorovinyl-trifluoromethyl ether of the formula $CF_2=CF-O-CF_3$, which is difficult to synthesize.

It is furthermore known that the exchange of a hydroxy group in primary and secondary aliphatic alcohols and in aliphatic carboxylic acids against a fluorine atom can be effected by reacting the mentioned alcohols or carboxylic acids with N-(1,1,2-trifluoro-2-chloroethyl)-diethylamine or -piperidine with formation of alkyl fluorides or acid fluorides according to the reaction scheme (1) [F. Liska, Chem. Listy 66, 189 (1972)].

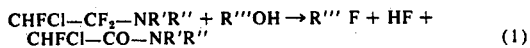

$$R' = R'' = C_2H_5, R'-R'' = -(CH_2)_5-, R''' = \text{Alkyl, Carboxy.}$$

In this reaction, the carbonyl, ester or amino groups in the radical R''' adjacent to the hydroxy group do not hinder the exchange of OH against F. Adjacent halogen atoms, on the other hand, have a different influence on the substituents which depends on their negative electron charge. For example, the reaction according to reaction scheme (1) for $C_6H_5CH(OH)-CHBr_2$ proceeds, as expected, with formation of $C_6H_5-CHF-CHBr_2$. However, with $C_6H_5-CH(OH)-CCl_3$, which contains the strongly electron-attracting trichloromethyl group in the α-position to the hydroxy group, esterification to $C_6H_5-CH(OCOCHFCl)-CCl_3$ occurs under otherwise equal reaction conditions [E. D. Bergmann and A. M. Cohen, Israel J. Chem. 8, 925 (1970)].

The present invention provides 1,2,2,2-tetrafluoroethyl ethers of the general formula I

in which R represents a straight chain or branched alkyl radical of 1 to 6 carbon atoms, the radical $-CH_2C-H_{3-n}X_n$, n being an integer of 1 to 3, and X being fluorine and/or chlorine, or the radical $-(CH_2)_m-OCHF-CF_3$ in which m is an integer from 2 to 4.

Radicals will contain 1 to 4, in particular 1 to 2, carbon atoms, preferably methyl and ethyl, are preferred.

The invention furthermore relates to a process for preparing the said 1,2,2,2-tetrafluoroethyl ethers which comprises a. reacting a fluoral-semi-acetal of the general formula II

in which R has the meaning given for it in formula I with an amine of the general formule III

in which R' and R'', which may be identical or different, represent straight chain or branched alkyl radicals of 1 to 6 carbon atoms or the cyclohexyl radical, or in which R' and R'' together may form an alkylene radical of 4 to 5 carbon atoms in which the carbon chain may also be interrupted by an oxygen atom, or b. reacting a fluoral-semi-acetal of the general formula II with sulfur tetrafluoride, or c. fluorinating a 1,2,2,2-tetrahalogenoethyl ether of the general formula IV

in which R has the meaning given for formula I, u is 0 or 1, and n is 1 or 2, preferably 2, if u is 1, and 1 to 3, preferably 2 or 3, if u is 0, in particular with hydrogen fluoride in the presence of a fluorination catalyst, or d. allowing a 2,2,2-trihalogeno-1-chloroethyl ether of the general formula V

in which R has the meaning given for formula I and n is 1 to 3, preferably 2 or 3, to react with mercury difluoride and, if n is 1 or 2, further reacting the reaction product according to method (c).

Method (a) is preferred.

The invention furthermore relates to inhalation anesthetics which contain a compound of the formula I, the use of the compounds of the formula I as inhalation anesthetics and a process for anesthetizing living beings with the use of compounds of the formula I.

The reaction according to method (a) proceeds according to reaction scheme (2):

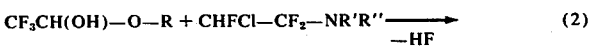

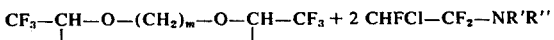

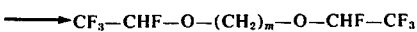

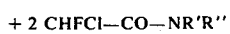

This reaction was unexpected, for several reasons. According to previous experience [C. T. Mason, C. C. Allain, J. Am. Chem. Soc. 78, 1682 (1956)], it had to be expected that the substitution of OH-groups in acetals by fluorine with formation of ethers monofluorinated in the α-position was not possible. Furthermore, it was known that semi-acetals are catalytically split in the presence of acids into the corresponding aldehydes and alcohols; thus, the splitting of the fluoral-semi-acetals of the formula II by the catalytic action of the hydrogen fluoride formed according to reaction scheme (2) into fluoral and the corresponding alcohols was to be expected, whereupon alkyl-fluorides should be obtained according to reaction (1), and not 1,2,2,2-tetrafluoroethyl ethers according to reaction (1), and not 1,2,2,2-tetrafluoroethyl ethers according to reaction (2).

Moreover, it was surprising that the reaction according to reaction scheme (2) yielded 1,2,2,2-tetrafluoroethyl ethers (I), although the very strongly electron-attracting trifluoromethyl group is adjacent to the OH-group, as the latter is present in the fluoral-semi-acetals of the formula (II), and an esterification to $CF_3$—CH(OCOCHFCl)—OR or $CF_3CH(OCOCHFCl)$—O—Y—O—CH(OCOCHFCl)$CF_3$ had to be expected.

The fluoral-semi-acetals of the formula II are prepared in known manner from the fluoral $CF_3CHO$ and the corresponding alcohols. The may also be obtained according to DT-OS 2,139,211 (German Patent application laid open to public inspection) from the hydrogen fluoride addition product of the fluoral, $CH_3CHO.HF$, by reaction with corresponding alcohols and subsequent elimination of the excess hydrogen fluoride by reaction with a Si-compound to form the volatile $SiF_4$. As alcohols, aliphatic, cyclic, aromatic and polyalcohols, as far as they are capable of forming semi-acetals, may be used. It is preferred to use methanol, ethanol, propanol, isopropanol, glycol, butanol, pentanol, hexanol and the corresponding branched alcohols, cyclohexanol, propylene glycol or the various butanediols as well as ethanol substituted once to thrice in the 2 position, such as chloro, difluoro, fluorochloro, dichloro, difluorochloro, dichlorofluoro, trichloro and, in particular, trifluoro, ethanol.

The amines of the formula III serving as fluorinating agents may be prepared in known manner from trifluorochloro-ethylene and secondary amines (L. H. Knox et al., J. Org. Chem. 29, (1964), 2187). With regard to the reactivity of the —$CF_2$— group, it is not critical which hydrocarbon radicals form the group R'R''.

Thus, there may be used as fluorinating agents: N-(1,1,2-trifluoro-2-chloroethyl)-dimethylamine, -diethylamine,-dipropylamine, -dibutylamine, -dicyclohexylamine, -methylethylamine, -methylcyclohexylamine, -piperidine or -morpholine. N-(1,1,2-trifluoro-2-chloroethyl)-diethylamine or -piperidine are preferably used.

According to reaction scheme (2), 1 mole of $CF_3CH(OH)$—OR are reacted with 1 mole of CHFCl—$CF_2$—NR'R'' or 1 mole of $CF_3CH(OH)$—O—$(CH_2)_m$—O—CH(OH)—$CF_3$ with 2 moles of CHFCl—$CF_2$—NR'R'' to the 1,2,2,2-tetrafluoroethyl ethers (I). In order to obtain a higher yield, it is advantageous to use CHFCL—$CF_2$—NR'R'' in an excess of up to 100 molar %, preferably from 5 to 50 molar %, in particular from 10 to 30 molar %, of the equivalent amount.

The reaction of the invention may be carried out within a large temperature range, in general at temperatures in the range of from −30°C to +100°C, preferably in the range of from −10°C to +50°C.

The exothermic reaction, in which it is advantageous to remove the heat by stirring and cooling, also proceeds in the absence of solvents. In order to obtain a constant reaction rate, however, it is of advantage to add solvents such as methylene chloride, tetrahydrofurane, diethyl ether, di-isopropyl ether, di-n-butyl ether or di-n-hexyl ether. It is suitable to select the solvents according to their boiling point, permitting a good separation by distillation from the reaction product. With this point in view, diethyl ether or di-n-butyl ether have preferably been used.

The process of the invention is carried out, for example, by introducing an amine of the formula III with a solvent and adding dropwise, while stirring, the fluoral semi-acetal of the formula II. After the homogeneous reaction mixture has been allowed to stand for several hours at room temperature, the reaction product is washed with water in order to remove the hydrogen fluoride, then with a solution of bicarbonate until the reaction is neutral, whereby at the same time any excess of CHFCl—$CF_2$—NR'R'' is destroyed by reaction with the washing water. By separation of the aqueous phase and subsequent drying and distillation of the organic phase, the 1,2,2,2-tetrafluoroethyl ether of the invention is obtained.

The reaction according to method (b) proceeds according to the reaction scheme (3):

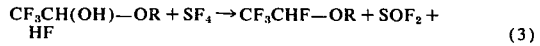

$$CF_3CH(OH)—OR + SF_4 \rightarrow CF_3CHF—OR + SOF_2 + HF \qquad (3)$$

In this reaction, preferably 1 mole of the fluoral-semiacetal is reacted at a temperature of 20° to 60°C with 1 to 1.5 moles, preferably 1.2 mole, of $SF_4$, while stirring, in an autoclave under the pressure of the sulfur tetrafluoride itself. The reaction time is about 24 hours. After removal of the gas, the liquid phase is washed with water and a solution of bicarbonate until it shows a neutral reaction and then dried and subjected to fractional distillation in the usual manner.

The reaction according to method (c) proceeds according to the reaction scheme (4):

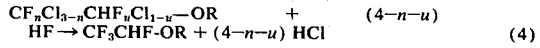

$$CF_nCl_{3-n}CHF_uCl_{1-u}—OR + (4-n-u) HF \rightarrow CF_3CHF-OR + (4-n-u) HCl \qquad (4)$$

The 1,2,2,2-tetrahalogeno-ethyl ether of the formula IV is passed, for example, together with a suitably higher than stoichiometric quantity of hydrogen fluoride, at a temperature of 150° to 350°C, over chromium oxy-fluoride as the catalyst. It is preferred to use 2 to 6 times the stoichiometric quantity of hydrogen fluoride. The reaction products are generally dissolved in the gaseous state in water in order to separate hydrohalic acids. The organic phase may be treated with a bicarbonate solution, dried in the usual manner and subjected to fractional distillation.

As catalysts, there may also be used, for example the antimony compounds known as fluorination catalysts; the process is then carried out in liquid phase and in an autoclave.

The starting products of the formula IV used for this method may be prepared, if u = 0, according or analogously to the method described by S. M. McElvain and M. J. Curry [J. Am. Chem. Soc. 70, 3784 (1948)] or in U.S. Pat. No. 2,870,219 by reacting a semiacetal of the formula VI $CF_nCl_{3-n}CH(OH)—OR$     (VI)

in an ethereal solution with thionyl chloride in the presence of pyridine. The semi-acetals of the formula VI may be prepared by the addition of a corresponding alcohol to monofluoro-dichloroacetaldehyde, difluoro-monochloroacetaldehyde and — as described above — trifluoroacetaldehyde (fluoral). In particular, there may be used as starting products of the formula IV with $u = 0$, for example:

1,2,2-trichloro-2-fluoroethyl-methyl ether, -ethyl ether, -n-propyl ether, -n-hexyl ether, -2'-chloroethyl ether, -2',2'-fluorochloroethyl ether, -2',2',2'-trifluoroethyl ether, glycol-1,2-bis(1,2,2-trichloro-2-fluoroethyl) ether, 1,2-dichloro-2,2-difluoroethyl-methyl ether, -ethyl ether, -isopropyl ether,-n-hexyl ether, -2'-chloroethyl ether, -2',2'-dichloroethyl ether, -2',2'-fluorochloroethyl ether, -2',2'-difluoroethyl ether, -2',2',2'-trifluoroethyl ether, glycol-1,2-bis(1,2-dichloro-2,2-difluoroethyl) ether, butanediol-1,3-bis(1,2-dichloro-2,2-difluoroethyl) ether, and 2,2,2-trifluoro-1-chloroethyl-methyl ether, -ethyl ether, -n-propyl ether, -isopropyl ether, -n-hexyl ether, -cyclohexyl ether, -2'-chloroethyl ether, -2',2'-dichloroethyl ether, -2',2'-chlorofluoroethyl ether, -2',2'-difluoroethyl ether, -2',2', 2'-dichlorofluoroethyl ether, -2',2',2'-difluorochloroethyl ether, -2',2',2'-trichloroethyl ether, -2',2',2'-trifluoroethyl ether, glycol-1,2-bis-(2,2,2-trifluoro-1-chloroethyl) ether, propyleneglycol-1,2-bis(2,2,2-trifluoro-1-chloroethyl) ether and butanediol-1,4-bis(2,2,2-trifluoro-1-chloroethyl) ether.

The starting compounds of the formula IV for method (c) may be prepared, if $m = 1$, in a manner analogous to that of methods (a) and (b) by reacting a semi-acetal of the formula VI with an amine of the formula III or with sulfur tetrafluoride. As starting products of the formula IV with $m = 1$, there may be used, for example:

1,2-difluoro-2,2-dichloroethyl-methyl ether, -ethyl ether, n-propyl ether, -n-hexyl ether, -2'-chloroethyl ether, -2',2'-chlorofluoroethyl ether, -2',2',2'-trifluoroethyl ether, glycol-1,2-bis-(1,2-difluoro-2,2-dichloroethyl) ether and 1,2,2-trifluoro-2-chloroethyl-methyl ether, -ethyl ether, -isopropyl ether, --n-hexyl ether, -2'-chloroethyl ether, -2',2'-dichloroethyl ether, -2',2'-chlorofluoroethyl ether, -2',2'-difluoroethyl ether, -2',2',2'-trifluoroethyl ether, glycol-1,2-bis-(1,2,2-trifluoro-2-chloroethyl) ether and butanediol-1,3-bis-(1,2,2-trifluoro-2-chloroethyl) ether.

The reaction according to method (d) proceeds according to the reaction scheme (5):

$2\ CF_nCl_{3-n}CHCl—OR + HgF_2 \rightarrow CF_nCL_{3-n}CHF—OR + HgCl_2$   (5)

For example, about 2 moles of the 2,2,2-trihalogeno-1-chloroethyl ether of the formula V are added slowly, with vigorous stirring, to 1 mole of $HgF_2$. The reaction temperature is in the range of from 0° to +50° C, preferably at room temperature.

The $HgCl_2$ formed during the reaction is filtered off and the reaction product is submitted to fractional distillation.

The starting products of the formula V for method (d) are identical with those of the formula IV with $u = 0$.

The products $CF_nCl_{3-n}CHF—OR$ obtained by the reaction of compounds of the formula V with $HgF_2$ are reacted in the cases $n = 1$ and $n = 2$ according to method (c) to the final products of the formula I of the invention.

According to the invention, there may be obtained, for example, the following 1,2,2,2-tetrafluoroethyl ethers of the formula I:

1,2,2,2-tetrafluoroethyl-methyl ether, -ethyl ether, -n-propyl ether, -isopropyl ether, -n-butyl ether, -n-hexyl ether, -cyclohexyl ether, -2'-chloroethyl ether, -2',2'-dichloroethyl ether,-2',2'-chlorofluoroethyl ether, -2',2'-difluoroethyl ether, -2',2',2'-trichloroethyl ether, -2',2',2'-dichlorofluoroethyl ether, -2',2',2'-chlorodifluoroethyl ether, -2',2',2'-trifluoroethyl ether, glycol-1,2-bis(1,2,2,2-tetrafluoroethyl) ether, propanediol-1,2-bis-(1,2,2,2-tetrafluoroethyl) ether, butanediol-1,2-bis-(1,2,2,2-tetrafluoroethyl) ether and butanediol-1,4-bis-(1,2,2,2-tetrafluoroethyl) ether.

The 1,2,2,2-tetrafluoroethyl ethers of the invention are colorless, easily mobile liquids with a faint agreeable odour. They are completely miscible with other organic liquids and have a good dissolving power, especially for fluorinated olefins and other fluorine-containing organic compounds.

The physical properties and spectroscopic data of the compounds of the invention of the formula (I) $CF_3CHF—OR$ with $R = CH_3$ or $C_2H_5$ are compiled in Table 1.

Table 1

| Compound | $CF_3CHF—OCH_3$ | $CF_3CHF—OC_2H_5$ |
|---|---|---|
| Molecular weight | 132 | 146 |
| Boiling point (°C) | 38–39/768 mm | 56–58/766 mm |
| $^1H$—NMR—Spectrum | $\delta = 3,68$ ppm (d,J = 3Hz,CH₃) | $\delta = 1,30$ ppm (t,J = 7Hz,CH₃) |
| | $\delta = 5,32$ ppm (dq,J_d = 61Hz, J_q = 3Hz,CH) | $\delta = 3,91$ ppm (m,J = 3Hz,CH₂) |
| | | $\delta = 5,37$ ppm (dq,J_d = 61 Hz Jq = 3Hz,CH) |

The compounds of the invention may be used as inhalation anesthetics. They are difficult to ignite under normal conditions and stable to the so-called breathing lime which is usually employed in anesthesia apparatuses for the absorption of $CO_2$ from the breathing air and which consists, for example of a mixture of Ca-$(OH)_2$ and $Ba(OH)_2$.

Their great stability is surprising, since even known compounds of analogous constitution such as $CCl_3CHCl—OCH_3$ and $CCl_3CHF—OCH_3$ are very reactive α-halogen ethers which are not stable to acids and to bases.

The compounds of the invention may also be used as intermediate products for the preparation of other anesthetics.

In particular, the easily volatile lower homologues $CF_3CHF—OCH_3$ and $CF_3CHF—O—C_2H_5$, and the derivatives of the last-mentioned compounds which are fluorinated twice or thrice in the 2-position of the ethyl group, have a very good anesthetising action on anesthetisable living beings.

Owing to their relatively low boiling point the compounds can be admixed in simple and controllable manner to breathing mixtures which secure the maintenance of life during anesthesia by a sufficient concentration of oxygen.

The action of the ethers of the invention as inhalation anesthetics is proved by the results of a pharmacological test in which the compound $CF_3CHF-O-CH_3$ was compared with diethyl ether.

In this pharmacological test, groups of 4 mice each were exposed in a closed glass bell of a capacity of 26 liters to anesthesia mixtures produced by evaporation of the (1,2,2,2-tetrafluoro-ethyl)-methyl ether of the invention or diethyl ether in various quantities. The animals were left in the gas room each time for a period of 10 minutes. The course of the anesthesia and the awakening of the animals were observed.

In the following table 2, the time $t_I$ until the begin of the tolerance stage and the time $t_{II}$ until the awakening of the mice is indicated in dependence on the concentration of the anesthetic (ml of evaporated liquid per 26 liters of air).

Table 2

| Substance | 5.0 ml/26 Ltr. | | 7.5 ml/26 Ltr. | | 10.0 ml/26 Ltr. | |
|---|---|---|---|---|---|---|
| | $t_I$ | $t_{II}$ | $t_I$ | $t_{II}$ | $t_I$ | $t_{II}$ |
| $CF_3CHF-OCH_3$ | | | 3'05" | 2'15" | 2'30" | 2'20" |
| $C_2H_5-O-C_2H_5$ (Comparative substance) | 4'50" | 3' | | | 2'50" | 5'30" |

A comparison of the test results shows that the ether of the invention is distinguished in particular by a more favorable shorter recovery time ($t_{II}$). Thereby, the risk of side effects caused by the anoxia occurring during anesthesia, in particular of the cardiac muscle and of the parenchymatous organs, especially of the liver, is considerably reduced.

The ethers of the invention may also be used together with other inhalation anesthetics, for example nitrous oxide or diethyl ether, furthermore with other anesthetic or therapeutic auxiliary agents, for example muscle relaxants, barbiturates and plasma expanders, as is often required in modern combination anesthesia.

The following Examples illustrate the invention:

EXAMPLE 1:

680 g (3.6moles) of N-( 1,1,2-trifluoro-2-chloroethyl)-diethylamine and 800 ml of anhydrous di-n-butyl ether were introduced into a four neck flask having a capacity of 2 liters and provided with thermometer, stirrer, dropping funnel and a reflux condenser cooled with ice-water, and then 390 g (3.0 moles) of fluoral-methyl-semi-acetal were added dropwise within 3 hours at 0° C. The mixture was then allowed to slowly warm to room temperature and, after standing overnight, it was washed with water and bicarbonate solution in order to remove the hydrogen fluoride. After drying with magnesium sulfate and phosphorus pentoxide, the 1,2,2,2-tetrafluoroethyl-methyl ether was distilled off over a packed column.

Yield: 272 g = 68.5% of the theory; B.p. 38° – 39°C/768 mm. $CF_3CHF-O-CH_3$    MW 132.

Analysis: Calc.: C, 27.3%; H, 3.0%; F, 57.7%. Found: C, 27.5%; H, 3.0%; F,57.5%.

EXAMPLE 2

481 g (2.4 moles) of N-(1,1,2-trifluoro-2-chloroethyl)-piperidine were mixed with 600 ml of anhydrous di-n-butyl ether in a four-neck flask of a capacity of 2 liters which was provided with a thermometer, dropping funnel, stirrer and a reflux condenser which was closed by a calcium chloride tube, and combined at 10°C within 2 hours with 288 g (2.0 moles) of fluoral-ethyl-semi-acetal. After the whole was allowed to stand overnight at room temperature, the hydrogen fluoride was removed from the product by washing with water and bicarbonate solution. The dried ether phase was subsequently subjected to fractional distillation. 164 g (56%) of 1,2,2,2-tetrafluoro-ethyl-ethyl ether were obtained; B.p. 56°–58° C/762 mm. $CF_3CHF-O-C_2H_5$    MW 146.

Analysis: Calc.: C, 32.8%; H, 4.1%; F, 52.0%. Found: C, 32.4%; H, 4.1%; F, 52.0%.

EXAMPLE 3

281 g (1.55 moles) of fluoral-2-chloroethyl-semi-acetal were introduced through a dropping funnel at 0°C within 3 hours into a solution of 330 g (1.76 moles) of N-(1,1,2-trifluoro-2-chloroethyl)-diethylamine in 600 ml of anhydrous diethyl ether. After the whole was allowed to stand overnight, the reaction product was washed with water and bicarbonate solution, dried with $MgSO_4$ and $P_2O_5$ and subjected to distillation. First, the diethyl ether was separated and then, at a boiling point of 110° – 111°C at 757 mm, the 1,2,2,2-tetrafluoroethyl-2'-chloroethyl ether with a yield of 213 g (76%).

$n_D^{20}$ = 1.3466. $CF_3CHF-O-CH_2CH_2Cl$    MW 180.5.

Analysis: Calc.: C, 26.6%; H, 2.8%; F, 42.0%; Cl; 19.6%. Found: C, 26.3%; H, 2.8%; F, 41.1%; Cl, 19.8%.

In analogous manner, there was obtained by the reaction of N-(1,1,2-trifluoro-2-chloroethyl)-diethylamine with fluoral-isopropyl-semiacetal: 1,2,2,2-tetrafluoro-ethyl-isopropyl ether; B.p 72° – 73°C/761 mm. Yield: 45%.

$n_D^{20}$ = 1.3104  $CF_3CHF-O-CH(CH_3)_2$    MW 160

Analysis: Calc.: C, 37.5% H, 5.0%; F, 47.5%. Found: C, 37.4%; H, 5.0%; F, 46.3%.

Starting from N-(1,1,2-trifluoro-2-chloroethyl)-diethylamine, there were furthermore obtained in analogous manner:

by reaction with fluoral-n-propyl-semiacetal, 1,2,2,2-tetrafluoroethyl-n-propyl ether, by reaction with fluoral-n-butyl-semiacetal, 1,2,2,2-tetrafluoroethyl-n-butyl ether, by reaction with fluoral-n-pentyl-semiacetal, 1,2,2,2-tetrafluoroethyl-n-pentyl ether, and by reaction with fluoral-n-hexyl-semiacetal, 1,2,2,2-tetrafluoroethyl-n-hexyl ether.

EXAMPLE 4

286 g (1.1 mole) of ethylene-glycol-bis-(fluoral-semiacetal) were added dropwise, within 3.5 hours, to a mixture of 418 g (2.2 moles) of N-(1,1,2-trifluoro-2-chloroethyl)-diethylamine and 500 ml of anhydrous diethyl ether. The reaction temperature was kept at 0°C by external cooling. After standing overnight, the product was washed with water and bicarbonate solution until it showed a neutral reaction, dried with $MgSO_4$ and $P_2O_5$, freed from diethyl ether by distillation under normal pressure and subjected to fractional distillation. 147 g (51%) of ethylene-glycol-bis(1,2,2,2-tetrafluoroethyl) ether were obtained; B.p. 69.5°C/29 mm.

$n_D^{20} = 1.3089$ $CF_3CHF-OCH_2-CH_2-O-CHFCF_3$
MW 262.

Analysis: Calc.: C, 27.4%; H, 2.3%; F, 58.0%. Found: C, 27.4%; H, 2.3%; F, 57.1%.

Starting from N-(1,1,2-trifluoro-2-chloroethyl)-diethylamine, there were obtained in analogous manner:

by reaction with propyleneglycol-bis-(fluoral-semiacetal), propyleneglycol-bis-(1,2,2,2-tetrafluoroethyl) ether;

by reaction with butane-1,4-diol-bis-(fluoral-semiacetal), the butane-1,4-diol-bis-(1,2,2,2-tetrafluoroethyl)-ether.

EXAMPLE 5

297 g (1.5 moles) of fluoral-2,2,2-trifluoroethyl-semiacetal were added dropwise, within 3 hours, to a solution of 341 g (1.8 moles) of N-(1,1,2-trifluoro-2-chloroethyl)-diethylamine in 400 ml of anhydrous di-n-butyl ester. After standing overnight at room temperature, the reaction product was washed with water and sodium bicarbonate solution, dried with $MgSO_4$ and $P_2O_5$ and distilled. 233 g (78%) of 1,2,2,2-tetrafluoroethyl-2',2',2'-trifluoroethyl ether were obtained.

$CF_3CHF-O-CH_2CF_3$   MW 200
B.p. 59° – 59.5°C/757 mm.

We claim:
1. A 1,2,2,2-tetrafluoroethyl ether of the formula

wherein R is methyl or ethyl.

2. A compound as in claim 1 which is

3. A compound as in claim 1 which is

* * * * *